(12) United States Patent
Chapman

(10) Patent No.: US 9,588,117 B2
(45) Date of Patent: *Mar. 7, 2017

(54) DETECTING CELLS SECRETING A PROTEIN OF INTEREST

(71) Applicant: Berkeley Lights, Inc., Emeryville, CA (US)

(72) Inventor: Kevin T. Chapman, Santa Monica, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/583,351

(22) Filed: Dec. 26, 2014

(65) Prior Publication Data

US 2015/0111784 A1    Apr. 23, 2015

Related U.S. Application Data

(63) Continuation of application No. 14/044,559, filed on Oct. 2, 2013, now Pat. No. 8,921,055.

(60) Provisional application No. 61/720,349, filed on Oct. 30, 2012.

(51) Int. Cl.
    *G01N 33/569* (2006.01)
    *G01N 33/68* (2006.01)

(52) U.S. Cl.
    CPC . *G01N 33/56972* (2013.01); *G01N 33/56911* (2013.01); *G01N 33/56961* (2013.01); *G01N 33/56966* (2013.01); *G01N 33/6854* (2013.01); *G01N 2458/00* (2013.01); *G01N 2469/10* (2013.01)

(58) Field of Classification Search
    None
    See application file for complete search history.

(56) References Cited

U.S. PATENT DOCUMENTS

| | | |
|---|---|---|
| 6,010,902 A | 1/2000 | Ledbetter et al. |
| 6,071,517 A | 6/2000 | Fanger et al. |
| 6,291,208 B1 | 9/2001 | Anand et al. |
| 6,448,075 B1 | 9/2002 | Thomas et al. |
| 6,958,132 B2 | 10/2005 | Chiou et al. |
| 7,030,228 B1 | 4/2006 | Schmitz et al. |
| 7,612,355 B2 | 11/2009 | Wu et al. |
| 7,956,339 B2 | 6/2011 | Ohta et al. |
| 8,304,195 B2 | 11/2012 | Hagen et al. |
| 2005/0221325 A1 | 10/2005 | Thill |
| 2006/0073095 A1 | 4/2006 | Kessler |
| 2006/0148012 A1 | 7/2006 | Brown et al. |
| 2008/0255004 A1 | 10/2008 | Neurauter et al. |
| 2009/0137017 A1 | 5/2009 | Bonyhadi et al. |
| 2010/0255496 A1 | 10/2010 | Schrader |
| 2011/0244477 A1 | 10/2011 | Dosenovic et al. |
| 2012/0024708 A1 | 2/2012 | Chiou et al. |
| 2012/0118740 A1 | 5/2012 | Garcia et al. |
| 2012/0325665 A1 | 12/2012 | Chiou et al. |

OTHER PUBLICATIONS

International Preliminary Report on Patentability, PCT Application Serial No. PCT/US2013/067324 (May 5, 2015) 8 pages.
Abstract of Wilber et al., "Antibody fragments in tumor pretargeting. Evaluation of biotinylated Fab' colocalizaiton with recombinant streptavidin and avidin," Bioconjugate Chemistry, vol. 7, No. 6, (1996).
Molema et al., "The use of bispecific antibodies in tumor cell and tumor vasculature directed immunotherapy," Journal of Controlled Release, vol. 64, No. 1 (Apr. 1998), pp. 229-239.
The International Search Report and the Written Opinion of the International Searching Authority, PCT Application Serial No. PCT/US2013/067324 (Jan. 16, 2014), 11 pages.
European Patent Office, Extended European Search Report for Application No. 13850928.6, dated Apr. 14, 2016.

*Primary Examiner* — Jacob Cheu
(74) *Attorney, Agent, or Firm* — Kenneth E. Horton; Kirton McConkie

(57) ABSTRACT

In some cases, the described systems and methods include obtaining a cell sample containing multiple antibody-producing cells. In such cases, the cells can be tagged with a cross-linking reagent having a first portion configured to bind to a marker on the antibody-producing cells and a second portion configured to bind to an antigen of interest. In some instances, the tagged antibody-producing cells are exposed to the antigen of interest such that the antigen becomes bound to the cells. In some such instances, the antibody-producing cells are also allowed to produce an antibody, such that a portion of the antibody-producing cells produce an antigen-specific antibody that binds to the antigen of interest. To identify cells that produce the antigen-specific antibody, the tagged cells can be exposed to a labeled secondary antibody that is configured to bind to the antigen-specific antibody. Other implementations are also described.

21 Claims, 11 Drawing Sheets

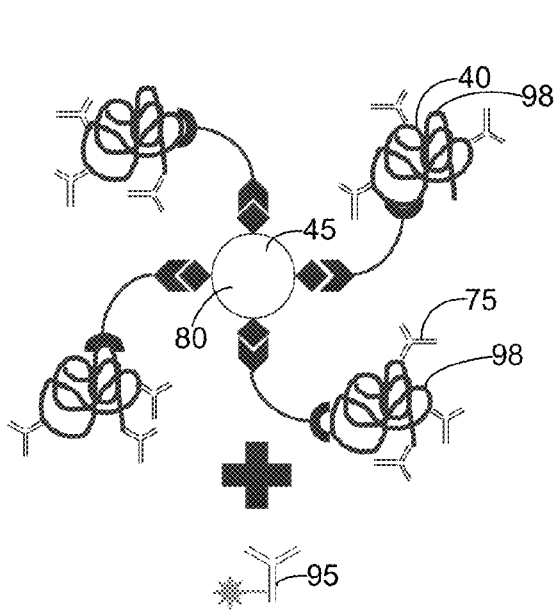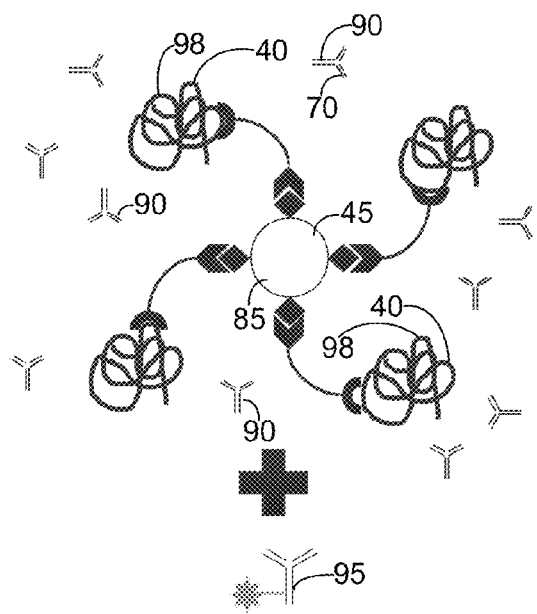
FIG. 4D
FIG. 4E
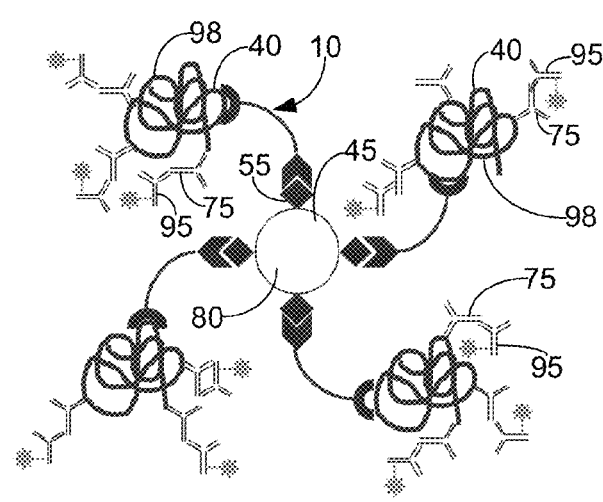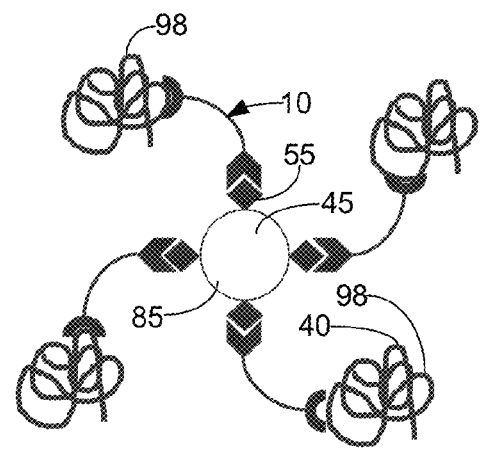
FIG. 4F
FIG. 4G

DETECTING CELLS SECRETING A PROTEIN OF INTEREST

CROSS REFERENCE TO RELATED APPLICATION(S)

This application is a division of U.S. patent application Ser. No. 14/044,559, filed Oct. 2, 2013 (pending), which is a non-provisional (and thus claims the benefit of the filing date) of U.S. provisional patent application Ser. No. 61/720,349 (filed Oct. 30, 2012). Both of the foregoing applications are incorporated by reference herein in their entireties.

BACKGROUND

Antibodies, which are also known as immunoglobulins, are proteins that are produced by B-cells and that are used by organisms' immune systems to identify and neutralize foreign objects, such as bacteria, viruses, and other antigens. Generally, antibodies include a Y-shaped protein having two large heavy chains and two small light chains. Additionally, while the general structure of antibodies is generally similar, a small region at the tip of such proteins can be extremely variable, allowing for millions of antibodies with slightly different tip structures, or antigen binding sites. The region of a Y-shaped antibody protein that includes the antigen binding site is sometimes called the $F_{AB}$ (or the fragment, antigen binding) region. This $F_{AB}$ region, in turn, includes a constant domain (which remains constant across multiple types of antibodies) and one or more variable or hypervariable regions (which vary from one antibody to another) from each heavy and light chain of the antibody. The variable domains from the heavy chain ("$V_H$") and light chain ("$V_L$"), which are part of the antibody's variable-region (or V-region), may be the most important parts of an antibody, and are responsible for binding the antibody to specific antigens.

While antibodies are well known for playing an important role in organisms' natural immune responses, antibodies have proven useful for a wide variety of other purposes. Indeed, antibodies have been found to be useful in many forms of medical diagnosis (e.g., in pregnancy tests, lupus diagnostic tests, etc.), in many research applications (e.g., to identify and locate intracellular and extracellular proteins), and even to treat a wide variety of diseases (e.g., rheumatoid arthritis, multiple sclerosis, psoriasis, cancer, etc.).

In the quest to find antibodies that can be used as therapeutic treatments for disease, there is a need to identify specific antibodies that are capable of effectively identifying and/or neutralizing antigens associated with a wide variety of diseases and maladies. Additionally, as many conventional methods for identifying such antibodies can be relatively inefficient and ineffective at identifying effective antibodies, it would be an improvement in the art to augment or even replace current techniques with other techniques.

SUMMARY

This disclosure relates to systems and methods for detecting cells that produce a protein of interest, such as an antigen-specific antibody. While the described methods can involve any suitable element, in some non-limiting implementations, the described methods include obtaining a cell sample containing protein-producing cells. In some cases, the protein-producing cells are then tagged with a cross-linking reagent, wherein the cross-linking reagent has a first portion that is adapted to bind to a cell surface marker that is specific to the protein-producing cells and a second portion that is configured to be bound to either an antigen of interest or a protein-specific antibody, which is an antibody that is specific to the protein of interest. In some such cases, the described methods further include exposing the protein-producing cells to the antigen of the interest or the protein-specific antibody, such that the protein-producing cells become linked through the cross-linking reagent to the antigen of interest or the protein-specific antibody. The described methods can further include allowing the protein-producing cells to produce the protein of interest, wherein the protein of interest is adapted to selectively bind with the antigen of interest or the protein-specific antibody. In some cases, the methods further include identifying cells that produce the protein of interest by exposing the protein-producing cells to a labeled antibody that is adapted to bind to the protein of interest.

In some other non-limiting implementations, the described methods include obtaining a cell sample containing multiple antibody-producing cells. In such cases, the antibody-producing cells can be tagged with a cross-linking reagent that has a first portion that is configured to bind to a marker that is specific to antibody-producing cells, and a second portion that is configured to bind to an antigen of interest. In some instances, the tagged antibody-producing cells are exposed to the antigen of interest such that the antigen becomes bound to the cells via the cross-linking reagent. The antibody-producing cells are also allowed to produce antibodies, such that a portion of the antibody-producing cells produce an antigen-specific antibody that binds to the antigen of interest. To identify cells that produce the antigen-specific antibody, the tagged cells can be exposed to a labeled secondary antibody that is configured to bind to the antigen-specific antibody.

In still other non-limiting implementations, the described methods include obtaining a cell sample containing protein-producing cells. In some cases, the protein-producing cells are tagged with a cross-linking reagent, wherein the cross-linking reagent has a first portion adapted to bind to a cell surface marker that is specific to the protein-producing cells and a second portion that is configured to be bound to an a protein-specific antibody, or an antibody that is specific to the protein of interest. In some cases, the described methods further include exposing the protein-producing cells to the protein-specific antibody, such that the protein-producing cells become linked through the cross-linking reagent to the protein-specific antibody. In some such cases, the protein-producing cells are also allowed to produce the protein of interest. Additionally, to identify cells that produce the protein of interest, the protein-producing cells are exposed to a labeled antibody that is adapted to bind to the protein of interest.

These and other features and advantages of the described systems and methods will be set forth or will become more fully apparent in the description that follows and in the appended claims. The features and advantages may be realized and obtained by means of the instruments and combinations particularly pointed out in the appended claims. Furthermore, the features and advantages of the described systems and methods may be learned by their practice or will be obvious from the description, as set forth hereinafter.

BRIEF DESCRIPTION OF THE DRAWINGS

FIGS. 4A-4G depict some alternative embodiments of the method for detecting cells that produce the protein of interest;

Figure 1:
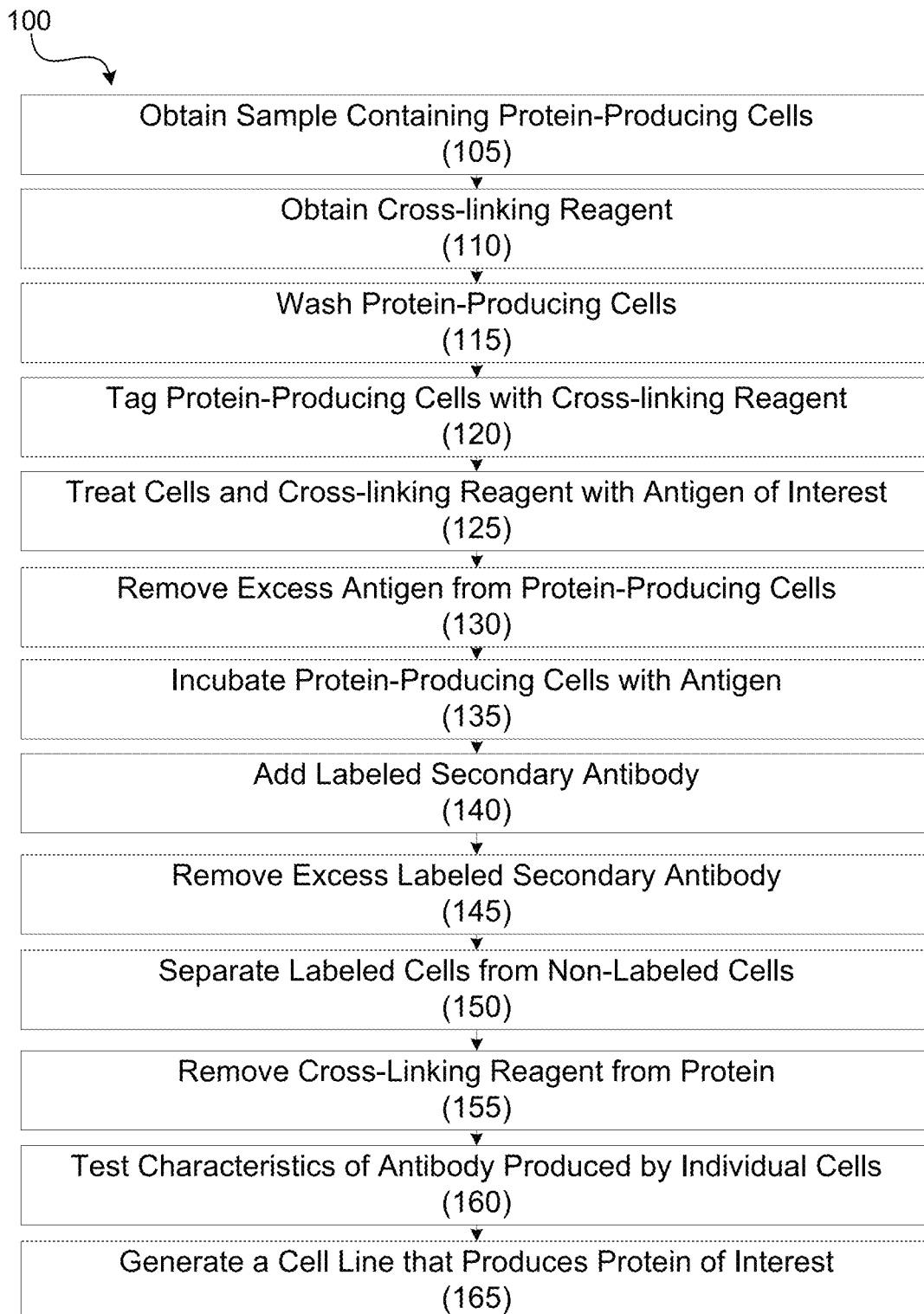
FIG. 1 shows a flowchart depicting some embodiments of a method for detecting cells that produce a protein of interest.

The Figures illustrate specific aspects of the described systems and methods for detecting cells secreting a protein of interest. Together with the following description, the Figures demonstrate and explain the principles of the structures, methods, and principles described herein. In the drawings, the thickness, size, and proportion of elements may be exaggerated or otherwise modified for clarity. Moreover, for clarity, the Figures may show simplified or partial views of the described methods and their associated components and reagents.

DETAILED DESCRIPTION

The following description supplies specific details in order to provide a thorough understanding. That said, to avoid obscuring aspects of the described systems and methods for detecting cells secreting a protein of interest, well-known structures, materials, processes, techniques, and operations are not shown or described in detail. Additionally, the skilled artisan will understand that the described systems and methods can be implemented and used without employing these specific details. Indeed, the described systems and methods can be placed into practice by modifying the illustrated methods and reagents and can be used in conjunction with any other apparatus and techniques conventionally used in the industry. For example, while the description below focuses on methods that include the use of cross-linking reagents, labeled secondary antibodies, labeled antibodies, beads and/or cells having an antigen (or antibody or other protein) of interest on their surface, and other devices and process, the described systems and methods (or portions thereof) can be used with any other suitable reagents, devices, or techniques. For instance, instead of (or in addition to) using the described systems and methods to detect cells that produce an antigen-specific antibody, the described systems and methods can be modified to allow for the detection of cells that produce any other suitable protein of interest.

As mentioned above, some embodiments of the described systems and methods relate to systems and methods for detecting cells that produce a protein of interest, such as an antigen-specific antibody. While the described methods can involve any suitable element, in some cases, they include obtaining a cell sample containing multiple antibody-producing cells. In such cases, the antibody-producing cells can be tagged with a cross-linking reagent that has a first portion that is configured to bind to a marker that is specific to antibody-producing cells, and a second portion that is configured to bind to an antigen of interest. In some instances, the tagged antibody-producing cells are exposed to the antigen of interest such that the antigen becomes bound to the cells via the cross-linking reagent. In some such instances, the antibody-producing cells are also allowed to produce an antibody, such that a portion of the antibody-producing cells produce an antigen-specific antibody that binds to the antigen of interest. To identify cells that produce the antigen-specific antibody, the tagged cells can be exposed to a labeled secondary antibody that is configured to bind to the antigen-specific antibody.

The described systems and methods thus generally provide techniques for detecting cells that produce a protein of interest, such as an antibody that binds to an antigen of interest (or an antigen-specific antibody). In this manner, the described systems and methods can be used to identify and/or separate cells that produce a protein (e.g., antibody) having a desired characteristic from cells that do not produce the protein of interest. Accordingly, some embodiments of the described systems and methods can be used to identify cells that produce an antigen-specific antibody that can be used in therapeutic treatments, in disease diagnosis, and/or for any other suitable application.

Figure 4A:
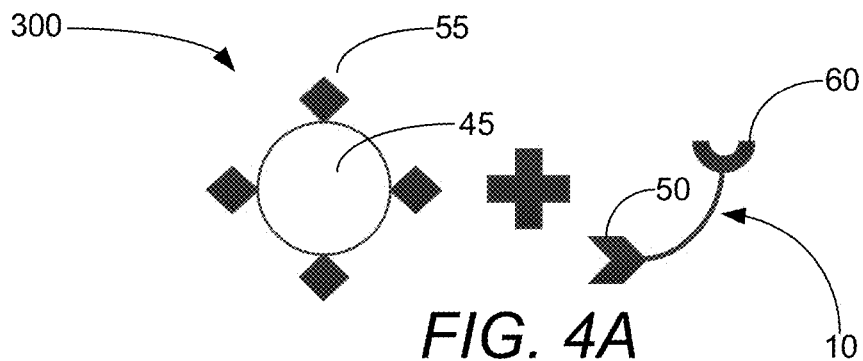
Figure 4B:
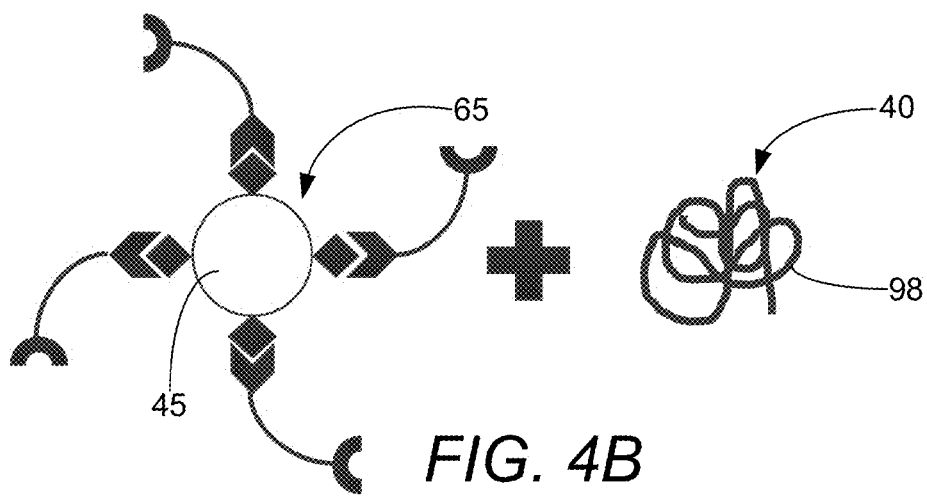
Figure 4C:
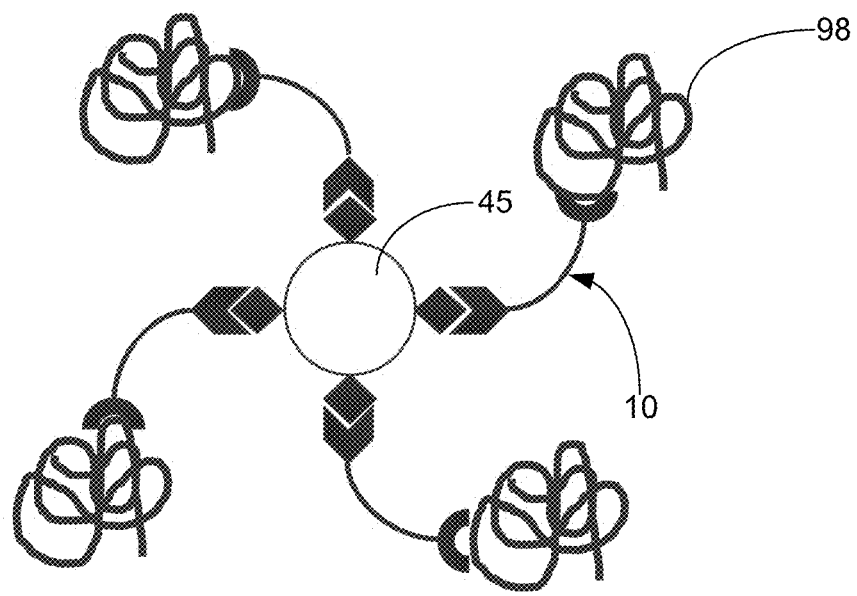
Figure 5A:
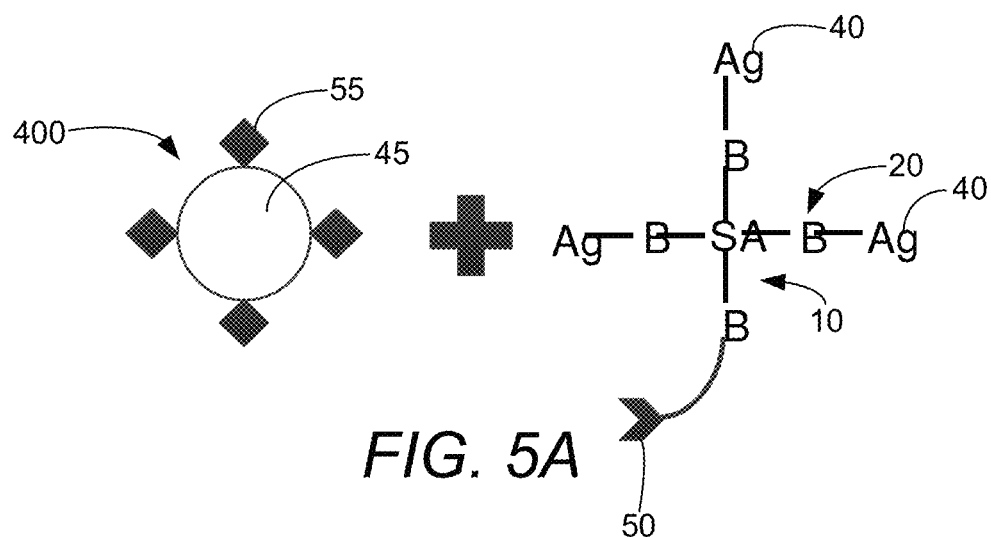
FIGS. 5A-5F depict some alternative embodiments of the method for detecting cells that produce the protein of interest.
Figure 5B:
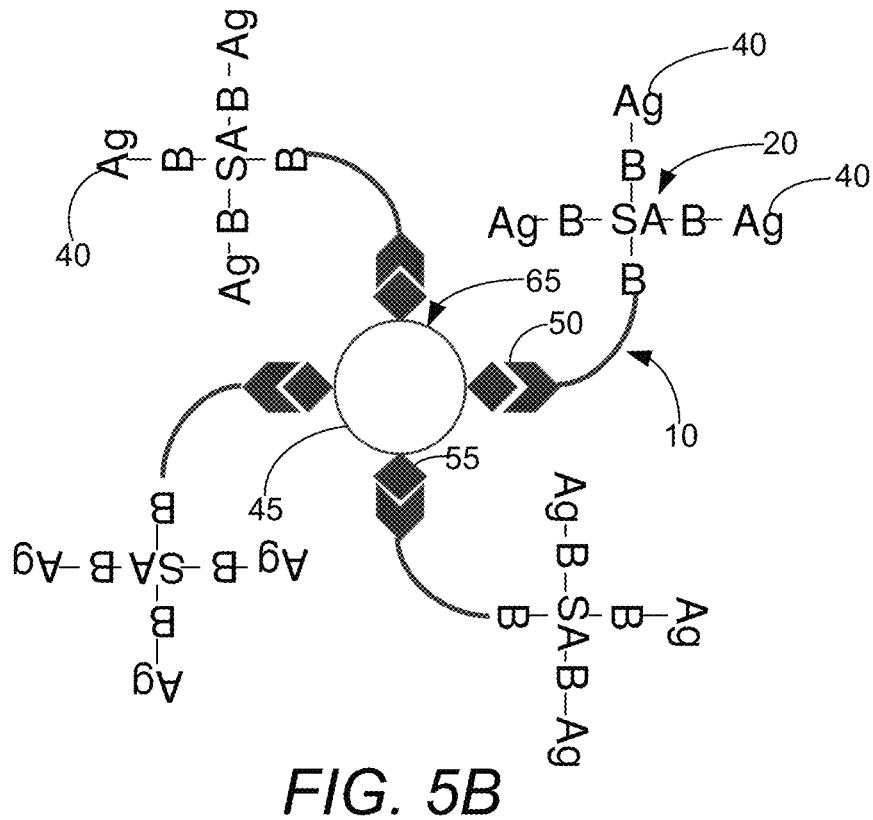
Figures 5C, 5D, 5E, 5F:
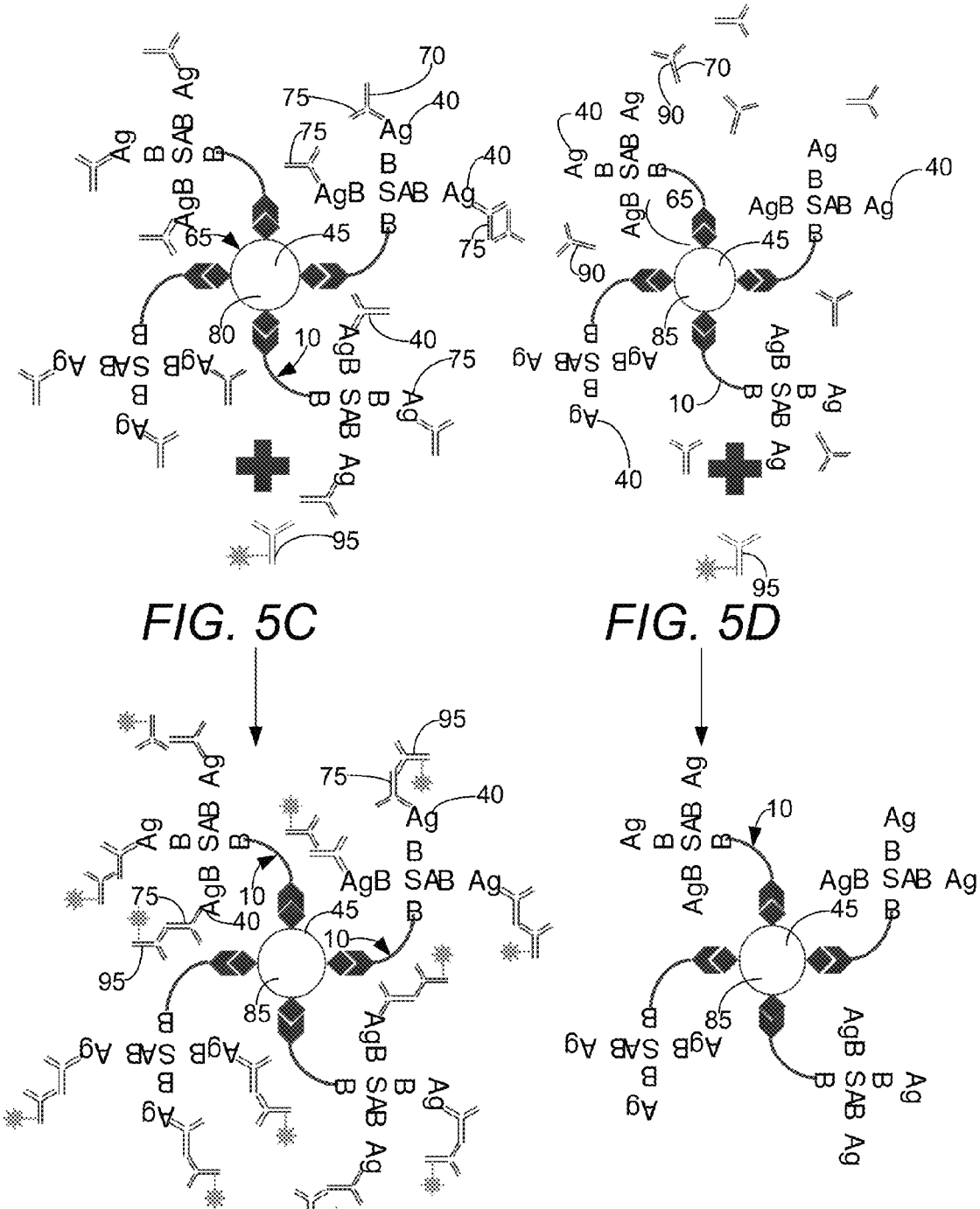
Figure 6:
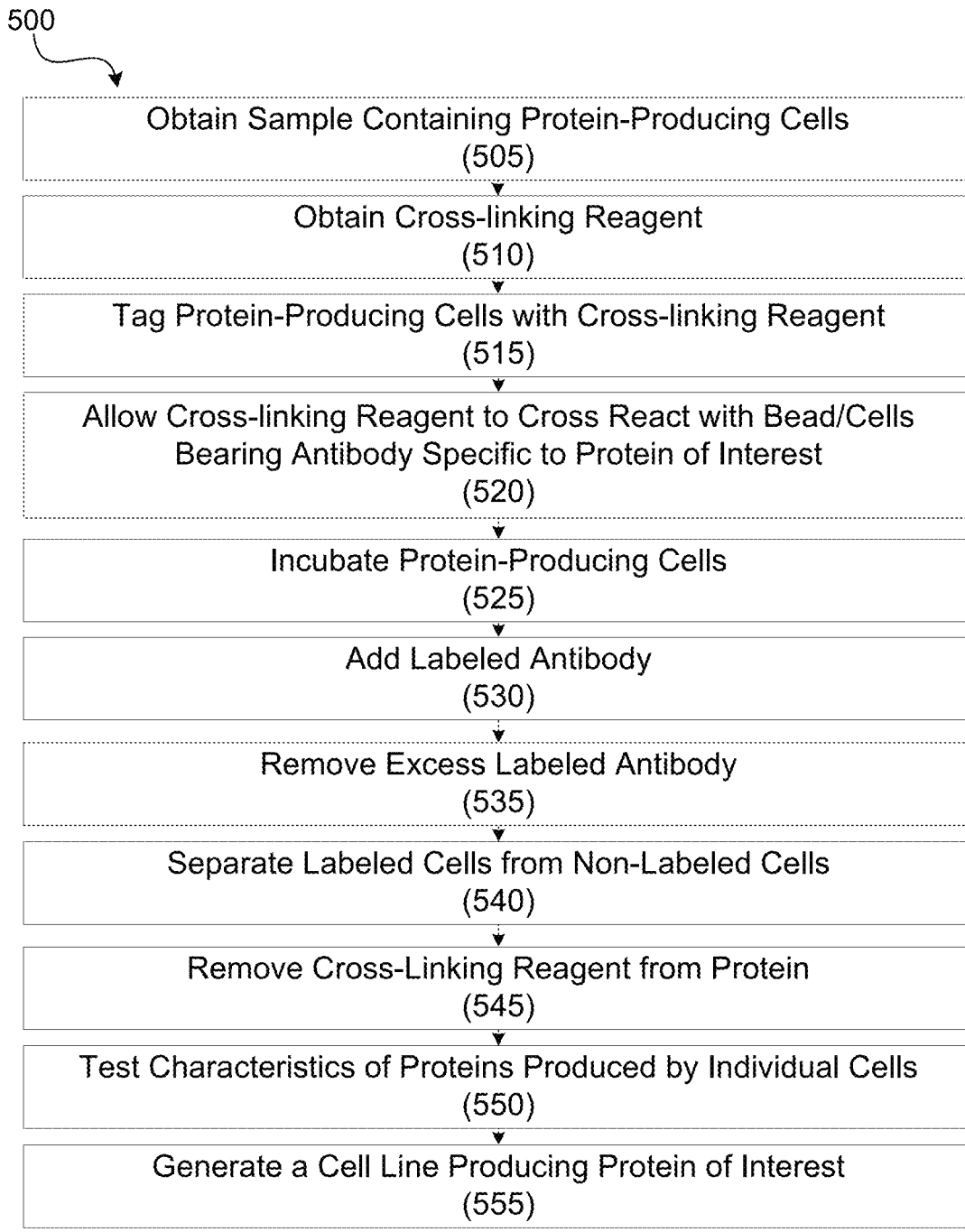
FIG. 6 shows a flowchart depicting some alternative embodiments of the method for detecting cells that produce the protein of interest.

While the described methods can be used and accomplished in any suitable manner, FIGS. 1 and 3A through 7F illustrate some embodiments of suitable methods for detecting cells that secrete a protein of interest (e.g., an antigen-specific antibody and/or another desired protein). In this regard, FIGS. 1 and 6 provide general overviews of some embodiments of the described methods, and FIGS. 3A through 5F and 7A through 7F provide illustrations of some more-specific embodiments of the described methods. To provide a better understanding of the described methods, the method 100 of FIG. 1 is first described, followed by a description of the methods in FIGS. 3A through 7F.

Each of the methods described herein can be modified in any suitable manner (including by rearranging, adding to, removing, substituting, and otherwise modifying various portions of the methods). Moreover, in some embodiments, at any suitable place in the methods, cells can be selected, moved, sorted, and/or the like through the use of opto-electrical techniques, such as opto-electrical wetting ("OEW") as disclosed, for example, in U.S. Pat. No. 6,958,132; opto-electronic tweezers ("OET") as disclosed, for example, in U.S. Pat. No. 7,612,355; cell shooting; and/or any other suitable technique that can be used to select, move, sort, filter, or otherwise manipulate cells. In this regard, an example of a cell shooter device is disclosed in U.S. Provisional Patent Application Ser. No. 61/653,322, filed May 30, 2012 (hereinafter the "'322 Application"), which is incorporated by reference herein in its entirety. Indeed, the sorting, selecting, moving, and/or the like of the cells can be performed, for example, in the processing/outputting device 100 of the '322 Application in the same way that the cells 120 are sorted, selected, moved, and/or the like in the device 100 as shown in the Figures of the '322 Application. Moreover, one or more of the cells can then be expressed in a droplet of medium as a cell 120 is expressed in a droplet 706 as illustrated in and discussed with respect to FIGS. 7A-11 of the '322 Application. Accordingly, in some embodiments, the cells can thus be transferred during one or more of the described steps of the instant application from one device to another, generally as illustrated in FIGS. 12-15 of the '322 Application.

Now, with reference to FIG. 1, that Figure shows (at 105) that some embodiments of the method 100 begin by obtaining a sample of protein-producing cells. In this regard, the term protein-producing cell may refer to any cell that is capable of secreting, displaying on its membrane, or otherwise producing a protein, such as a hormone, enzyme, functional protein, structural protein, and/or antibody. For the sake of simplicity, however, the method 100 of FIG. 1 focuses on protein-producing cells that produce an antibody (or antibody-producing cells). Some examples of such antibody-producing cells include, but are not limited to, B-lymphocytes, plasma cells, plasmablasts, hybridomas, activated B cells, memory cells, transformed cells, mammalian cells that express immunoglobulin genes or parts thereof, and/or any other cells that are able to produce an antibody.

While the sample of antibody-producing cells can be collected in any suitable manner and from any suitable location, in some embodiments, cells of a B-Cell lineage are surgically extracted (or otherwise removed) from an animal's spleen, lymphatic tissue, bone marrow, blood, and/or other suitable tissue or fluid. In this regard, any suitable number of cells can be collected.

With continued reference to FIG. 1 (at 105), in some embodiments, at least some of the cells in the sample of antibody-producing cells have been involved in an immune response. While this immune response can be triggered in any suitable manner, in some embodiments, an animal (e.g., a human, rabbit, rat, mouse, goat, cow, chimpanzee, monkey, or other organism); tissue; or cell population is exposed to an antigen of interest (e.g., via immunization, pathogen infection, pathogenesis, an auto-immune reaction, and/or a similar method) or is already suffering from a disease or pathological condition of interest. In this regard, and as used throughout this specification, the term antigen may refer to any known or unknown substance that can be recognized by an antibody, including, without limitation, any suitable protein, glycoprotein, and/or carbohydrate. In one example, an antigen is a biologically-active protein, such as one or more hormones, cytokines, and their cell receptors; bacterial or parasitic cell membranes or purified components thereof; and/or viral components. Additionally, while antigens can be in any suitable form, in some cases, antigens are available in a pure form obtained either by direct purification from the native source or by recombinant expression and purification of such antigens. In other cases, antigens are expressed on the surface of a cell, either naturally or recombinantly. In such cases, antigen expression can occur on, but is not limited to, mammalian cells, immunomodulatory cells, lymphocytes, monocytes, polymorphs, T cells, tumor cells, yeast cells, bacterial cells, infectious agents, parasites, plant cells, transfected cells (e.g., NSO, CHO, COS, 293 cells, etc.), cells associated with a particular disease or malady, and/or any other suitable cell or population of cells.

Figure 2A:
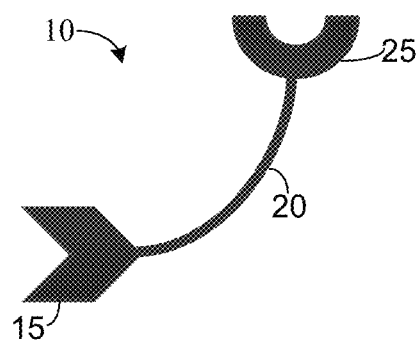
FIGS. 2A-2B each illustrate some embodiments of a cross-linking reagent.
Figure 2B:
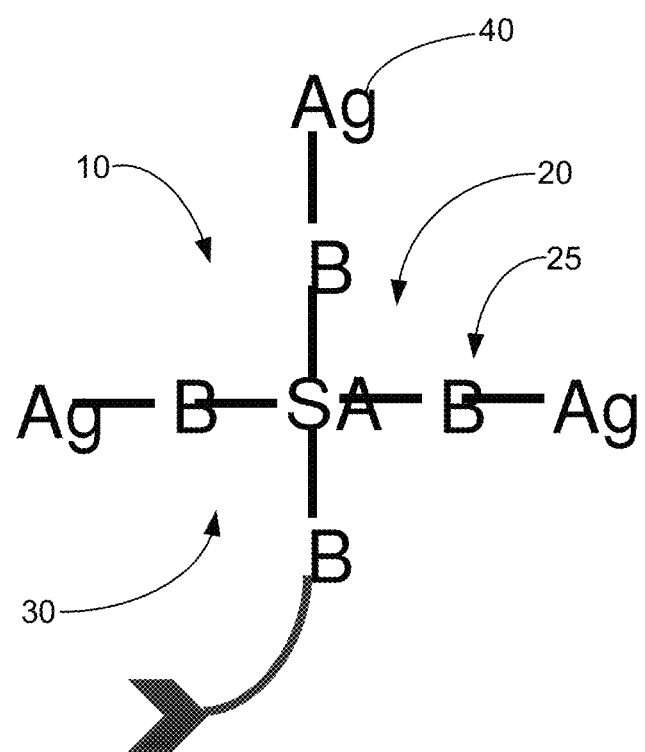

Continuing with the method 100, FIG. 1 (at 110) shows that, in some embodiments, the method 100 includes the preparation (or acquisition) of one or more cross-linking reagents. Such cross-linking reagents can comprise any suitable component and can be prepared in any suitable manner that allows a first portion of the cross-linking reagent to bind to a cell surface marker on an antibody-producing cell and a second portion of the reagent to bind to an antigen of interest. By way of illustration, FIGS. 2A and 2B show some embodiments in which the cross-linking reagent 10 comprises a first portion 15, a cross-linker 20, and second portion 25.

With respect to the first portion 15 of the cross-linking reagent 10, the first portion can comprise any suitable component that allows it to bind to a cell surface marker that is specific to a desired cell type. In this regard, the term cell surface marker may be used to refer to any protein expressed on a surface of a protein-producing cell (e.g., an antibody-producing cell) that is capable of being used to differentiate a cell expressing that protein from another cell that does not express the same protein. For instance, some examples of plasma cell surface markers include, but are not limited to, CD138, CD38, CD78, and the interleukin-6 receptor.

While the first portion 15 of the cross-linking reagent 10 can be made in any suitable manner, in some embodiments, an antibody that is specific to a cell surface marker (e.g., CD138) that is expressed on the surface of a desired protein-producing cells (e.g., or antibody-producing cell, such as a plasma cell) is obtained. In some embodiments, a $F_{AB}$ fragment (which may be used herein to refer to $F_{AB}$ fragments, $F_{AB}'$ fragments, and/or $F(_{AB}')_x$ fragments) of that antibody is then prepared and purified. In this regard, the $F_{AB}$ fragment of the antibody can be prepared in any suitable manner, including by using one or more enzymes (e.g., papain, pepsin, an immunoglobulin degrading enzyme from *Streptococcus pyogenes*, a proteolytic enzyme, etc.) to cleave the antibody and produce one or more $F_{AB}$ fragments. In some optional embodiments, to make the first portion of the cross-linking reagent, the variable regions of the heavy and light chains of the antibody are fused together to form a single-chain variable fragment ("scFv") that is about half the size of its corresponding $F_{AB}$ fragment, and that retains the original specificity of the parent antibody.

With regards to the cross-linker 20, the cross-linker can comprise any suitable chemical and/or biological linking agent having at least two reactive end groups that react with functional groups (e.g., primary amines, carboxyls, carbonyls, and/or sulfhydryls). Some examples of such linking agents include, but are not limited to, one or more hetero-bifunctional reagents, homo-bifunctional reagents, avidin-biotin cross-linkers, and streptavidin-biotin cross-linkers. According to some embodiments, however, FIG. 2B shows the cross-linker 20 comprises a streptavidin-biotin cross-linker 30 (wherein SA stands for streptavidin and B stands for biotin).

Turning now to the second portion 25 of the cross-linking reagent 10, the second portion can comprise any suitable component that allows it to bind to an antigen of interest and/or to a cell or bead bearing an antigen (or antibody or other protein) of interest on the cell/bead's outer surface. Some examples of suitable components that can be used as the second portion of the cross-linking reagent include, without limitation, a $F_{AB}$ fragment that is specific to the antigen of interest (e.g., a $F_{AB}$ made from an antigen-specific antibody), a $F_{AB}$ fragment that is specific to another protein of interest (e.g., an antibody or other protein), an scFv that is specific to the antigen of interest (e.g., an scFv made from an antigen-specific antibody), a $F_{AB}$ fragment which binds to a cell surface marker that is specific to the cell expressing the antigen of interest on the cell's membrane surface, a cross-linker (e.g., cross-linker 30) that is capable of binding to the antigen of interest (e.g., the antigen (or Ag) 40 shown in FIG. 2B), and/or a cross-linker that is capable of binding to a cell and/or bead bearing a protein (e.g., an antibody) of interest. By way of illustration, FIG. 2A shows some embodiments in which the second portion 25 of the cross-linking reagent 10 comprises a $F_{AB}$ fragment that is specific to the antigen of interest. In contrast, FIG. 2B shows that, in some embodiments, the second portion 25 of the cross-linking reagent 10 and the cross-linker 20 are one and the same. Thus, FIG. 2B shows that the cross-linker 20 itself can act as the second portion 25 and be bound to the antigen of interest 40.

The cross-linking reagent 10 can be made in any suitable manner, including, without limitation, through derivitization of proteins (e.g., amine derivitization, disulfide formation, carboxylic acid derivitization, etc.), activated-ester-based coupling, biotinylation, and/or any other suitable method. In some embodiments, however, the first portion 15 (e.g., the first $F_{AB}$ fragment) and the second portion 25 (e.g., the second $F_{AB}$ fragment) of the cross-linking reagent are biotinylated, mixed at approximately a 1:1 ratio, and cross-linked with streptavidin. In such embodiments, a tetramer with a statistical mixture of the first and second portions (e.g., $F_{AB}$ fragments) is made.

Continuing with the method 100 and returning to FIG. 1, that Figure shows (at 115) that some embodiments of the method include washing the sample of antibody-producing cells to remove antibody that is free in solution. In this regard, the cells can be washed in any suitable manner, including, without limitation, by being rinsed and/or being placed in one or more baths (e.g., water baths, cell-support media baths, etc.), through filtration (e.g., light filtration, microfluidic filtration, etc.), OET, OEW, and/or any other suitable method that is capable of retaining the antibody-producing cells while allowing free-floating antibodies to be washed away.

At 120, FIG. 1 shows the antibody-producing cells are treated with any suitable amount (e.g., an excess) of the cross-linking reagent 10 that allows such cells to be tagged with that reagent. In this manner, the first portion 15 of the cross-linking reagent is able to bind to the cell surface markers (e.g., CD138) of antibody-producing cells, while leaving cells that lack the desired cell surface markers (e.g., non-antibody-producing cells) substantially untagged.

At 125, FIG. 1 shows that some embodiments of the method 100 continue as the sample of cells (including the antibody-producing cells that are tagged with the cross-linking reagent 10) is treated with the antigen of interest 40. While this can be done in any suitable manner, in some embodiments, an antigen of interest is bound to (or expressed on) the surface of cells that are exposed in excess to the tagged antibody-producing cells. In other embodiments, an antigen of interest is bound to the surface of beads (e.g., via a chromic-chloride coupling method, water-soluble-carbodiimide-coupling method, or other suitable method) and exposed, in excess, to the tagged antibody-producing cells. In still other embodiments, a free form of the antigen of interest (e.g., a form in which the antigen of interest is not bound to cells or beads, such as a purified form of the antigen) is added to the tagged antibody-producing cells. In yet other embodiments, the antigen of interest is already bound to the cross-linking reagent 10 (as shown in FIG. 2B) when the antibody-producing cells are tagged with the reagent. In any case, as a result of treating the tagged antibody-producing cells with an excess of the antigen of interest, the antibody-producing cells are bound through the cross-linking reagent to the antigen of interest (e.g., via antigen-coated cells, antigen-coated beads, free-floating antigens, and/or a cross-linker comprising the antigen of interest).

At 130, FIG. 1 shows that, in some embodiments, the excess antigen of interest (or the antigen that is not bound to the tagged antibody-producing cells via the cross-linking reagent 10 is removed. In this regard, the excess antigen (e.g., the excess antigen-coated cells, antigen-coated beads, free-floating antigen, and/or a cross-linking reagent comprising the antigen of interest) can be removed in any suitable manner, including, without limitation, through filtration with OET, light filtration, and/or another microfluidic filtration technique. In one example, OET is used to create a light comb with a tine having a width that is configured to retain large materials (e.g., antibody-producing cells complexed through the cross-linking reagent 10 with the cells/ beads displaying the antigen of interest, free floating antigen, etc.) while allowing small materials (e.g., excess antigen-coated cells/beads, free-floating antigens, cross-linking reagents, etc.) to be carried away by a flow of liquid.

At 135, FIG. 1 shows that, in some embodiments, the tagged antibody-producing cells that have been linked through the cross-linking reagent 10 to the antigen of interest (e.g., to antigen-coated cells, antigen-coated beads, free-floating antigen, and/or a cross-linking reagent comprising the antigen of interest) are incubated to allow the cells to produce antibodies. In this regard, antibodies that are specific to the antigen of interest (or antigen-specific antibodies) will bind preferentially to the antigen of interest (e.g., to the antigen that is bound to the antibody-producing cells through the cross-linking reagent and beads comprising the antigen, cells comprising the antigen, free-floating antigen, and/or antigens that are included in the cross-linking reagent). More specifically, the antigen-specific antibody will bind preferentially to the antigen surrounding the antibody-producing cells that secreted that antibody.

FIG. 1, at 140, shows that some embodiments of the method 100 continue as the antigen-specific antibodies that are bound to the antigen of interest are marked or otherwise labeled. In this regard, the term label, and variations thereof, may refer to any suitable probe, marker, or label that can be connected to an antibody and be used to distinguish structures that are bound to the label from those that are not. In this regard, some examples of suitable labels include, but are not limited to, luminescent labels, radiolabels, and fluorescent labels (e.g., Aqua, Texas-Red, FITC, rhodamine, rhodamine derivative, fluorescein, fluorescein derivatives, cascade blue, Cy5, phycoerythrin, etc.).

While the labeled secondary antibody can be used in any suitable manner, in some embodiments, the labeled secondary antibody is added, in excess, to the solution containing tagged cells that are linked to the antigen of interest (e.g., via the cross-linking reagent 10). Additionally, although the labeled secondary antibody can have specificity for any or all Antibodies—either in their entirety or for portions thereof (e.g., the $F_C$ region, a $F_{AB}$ region, etc.), in some embodiments, the labeled secondary antibody is specific to the $F_C$ portion of the heavy chain of antibodies. As a result, in such embodiments, the labeled secondary antibody can bind to any antibodies in the sample (including antigen-specific antibodies that are bound to the antigen of interest, as well as to those antibodies that do not bind to the antigen of interest). Thus, cells that produce the antigen-specific antibody will be bound to the antigen of interest (e.g., via the cross-linking reagent 10), which in turn is bound to the antigen-specific antibody, and which in turn is bound to the labeled secondary antibody.

Continuing with FIG. 1, that Figure shows (at 145) that in some embodiments, once the labeled secondary antibody has been bound with the antigen-specific antibody (and/or any other antibodies), the excess labeled secondary antibody and/or non-antigen-specific antibodies are optionally washed away. In this regard, the excess labeled secondary antibody that is not bound to the antibody-producing cells (e.g., via the antigen-specific antibody, which is bound to the antigen of interest, and which is bound to the antibody-producing cell through the cross-linking reagent 10) is optionally washed away, or otherwise separated from, the antibody-producing cells in any suitable manner. As a result, some, if not all, of the potential background noise will also be washed away.

At 150, FIG. 1 shows that, in some embodiments, the antibody-producing cells that produce the antigen-specific antibodies (and which are, therefore, labeled with the labeled secondary antibody) are separated from the remaining cells that do not produce the antigen-specific antibody (and which are not labeled to the same extent, if at all). In this regard, the cells producing the antigen-specific antibody can be separated from the remaining cells in any suitable manner that allows cells producing the antigen-specific antibody (or labeled cells) to be identified and be separated from the cells that are not labeled (or that are not labeled to the desired extent).

Some examples of suitable methods for separating the labeled cells from non-labeled cells include, but are not limited to, the use of OET, other OET-based methods, OEW, micromanipulation, laser capture, micro-pipetting, flow cytometry, etc. Additionally, in some non-limiting embodiments, labeled cells are placed in holding pens, such as the virtual holding pens 714, 716, 718, and 720 of the device 100 illustrated in FIG. 7C and throughout other Figures of U.S. Provisional Patent Application Ser. No. 61/720,956, filed Oct. 31, 2012 (hereinafter the "'956 Application"), which is incorporated by reference herein in its entirety. Thereafter, process 1100 of FIG. 11 of the '956 Application can optionally be performed to further identify and select the cells based on the cells' ability to produce the antibody of interest. As discussed in the '956 Application, the pens 714, 716, 718, and 720 can be virtual pens or physical pens. Moreover, if virtual pens, the virtual pens can be created, moved, and/or manipulated and the cells can be selected, moved, and/or manipulated within the device 100 of the '956 Application, for example, using OET techniques generally as illustrated in FIG. 2 of the '956 Application or similar such technologies.

Once the labeled cells are separated from the non-labeled cells, FIG. 1 (at 155) shows that, in some embodiments, the antigen of interest can be released from those cells that have been identified as producing the antigen-specific antibody. Thus, where the antigen of interest is bound to beads or cells, such beads and/or cells can be released from the gathered cells that produce the antigen-specific antibody (or collected cells). Similarly, where the antigen of interest is bound directly to the cross-linker 20 (as shown in FIG. 2B), the antigen can be released. While the antigen of interest can be removed from the collected cells in any suitable manner, in some embodiments, the collected cells are treated with a proteolytic enzyme (e.g., trypsin and/or any other suitable proteolytic enzyme), heated, treated with chemicals that cleave or remove the cross-linker 20, and/or otherwise treated to remove/cleave any suitable portion of the cross-linking reagent and/or antigen.

Once the cells that produce the antigen-specific antibody have been identified and separated from other cells that do not produce the antigen-specific antibody (or desired amounts thereof), FIG. 1 at 160 shows that the cells producing the antigen-specific antibody and/or the corresponding antigen-specific antibodies themselves are optionally tested to determine whether the antigen-specific antibody has one or more desired characteristics (e.g., biochemical activity, antigen-specificity, antibody-binding affinity, is produced at a desired quantity, is produced at a desired concentration, etc.). In this regard, the collected cells and/or the antigen-specific antibody they produce can be tested in any suitable manner, including, without limitation, through one or more biochemical assays (e.g., to test the ability of a candidate antibody to augment or disrupt a biochemical pathway of interest), antibody-binding affinity assays, antigen-specificity assays, etc. Additionally, while the collected cells that produce the antigen-specific antibody can be tested collectively, in some preferred embodiments, such cells and/or the antibody they produce are tested on an individual cell basis.

In some embodiments, the collected cells that produce the antigen-specific antibody are each tested for one or more desired characteristics in physical chambers. While these chambers can have any suitable component or characteristic, in some embodiments, the chambers are the same as, or similar to any of the cell interrogation devices 100, 100', 400, 800, and 800' and the cell apparatus 1000 illustrated in the Figures of and discussed in U.S. Provisional Patent Application Ser. No. 61/664,421, filed Jun. 26, 2012 (hereinafter the "'421 Application"), which is hereby incorporated in its entirety. As discussed therein and with reference to FIGS. 2 and 3 of the '421 Application, such devices 100, 100' can include a chamber 114 and/or 114' for holding a cell 204 in a medium 202. New medium 202 can be introduced through an inlet 110 and medium 202 containing secretions from the cell 204 can be extracted through an outlet 112 and analyzed.

Another example of the physical chambers into which a cell or cells can optionally be placed for testing at step 160 of FIG. 1 of the instant application includes the cell secretion detection devices 100 and 100' illustrated in the Figures of and discussed in U.S. Provisional Patent Application Ser. No. 61/709,408, filed Oct. 4, 2012 (hereinafter the "'408 Application"), which is incorporated by reference herein in its entirety. As discuss therein and with reference to FIGS. 1A-3 of the '408 Application, such devices can include a chamber 120 and/or 120' for holding a cell 128 in a medium 130 and a sensor 140 comprising one or more binding regions 142-148. As illustrated in FIGS. 5A-6 of the '408 Application, the medium 130 can comprise radiant labels 502 that bind to analytes 508 of interest secreted by the cell 128. By monitoring with a detector 160 (see FIG. 1D of the '408 Application) radiation of the binding regions 142-148 as the secreted analytes 508 bind to those regions 142-148, the secretion of the analytes 508 can be measured and/or analyzed.

As noted, the chambers into which the cells are optionally placed at step 160 can be the same as or similar to the devices noted above from the '421 Application or the '408 Application. If the devices of the '421 Application, step 160 of the instant application can be performed, at least in part, by extracting through the outlet 112 medium 202 and analyzing the secretions from the cell 204 in the extracted medium 202 (see FIGS. 2 and 3 of the '421 Application) generally as discussed in the '421 Application. If the devices of the '408 Application, step 160 of the instant application can be performed, at least in part, by detecting and analyzing radiation from the binding regions 142-148 of the sensor 140 as briefly discussed above and in accordance with the more detailed discussions in the '408 Application.

As another example, at step 160 of the FIG. 1 in the instant application, the labeled cells can be placed in cell interrogation devices in which the cells are held in a medium, which can further be tested for the presence of the desired antibody. Examples of such cell interrogation devices include the cell interrogation devices 100, 100', 400, 800, and 800' and the cell apparatus 1000 as illustrated in the Figures of and discussed in the '421 Application. Other examples of such cell interrogation devices include the cell secretion detection devices 100 and 100' as illustrated in the Figures of and discussed in the '408 Application. The foregoing cell interrogation devices of the '421 Application and the '408 Application can be operated generally in any manner discussed in the '421 Application or the '408 Application but to detect secretion by the cells of the antibody of interest.

At 165, FIG. 1 shows that, in some embodiments, after a desired biochemical activity and/or other characteristic (e.g., antibody-binding affinity, antigen-specificity, concentration, etc.) of the antigen-specific antibody produced by the collected cells has been measured, a cell line is optionally created that includes a portion of the DNA sequence (e.g., a copy of antibody V-region DNA sequence) from the collected cells that produce the antigen-specific antibody (or other protein of interest) having one or more desired characteristics. In this regard, such a cell line can be produced in any suitable manner. Indeed, in some embodiments a portion of the DNA sequence (e.g., a copy of the V-region DNA sequence) from the collected cells that produce the antigen-specific antibody (or other protein of interest) having one or more desired characteristics is optionally placed into a plasmid (e.g., a plasmid encoding an immunoglobulin constant region), which can be transfected into a cell line that will produce the desired antigen-specific antibody (or other protein). In some embodiments, the entire antibody (or other protein) genes from one or more of the collected cells are cloned and/or sequenced. In other preferred embodiments, the variable regions or portions thereof (e.g., the $V_L$ and/or $V_H$), which confer the desired specificity of the antibody, are cloned and/or sequenced, and then synthesized through any conventional technique to produce recombinant antibodies. In this regard, recombinant antibodies can take several forms, including, without limitation, intact immunoglobulins, chimeric antibodies, humanized antibodies, antigen binding fragments (e.g., Fc, $F_{AB}$, $F_{AB}'$, and $F(_{AB}')_x$ fragments, and derivatives thereof, such as scFv fragments).

Where the variable region of the DNA from the selected cells is cloned into a plasmid, the cloning process can be accomplished in any suitable manner. In some embodiments, however, the cloning process includes, lysing one of the collected cells (e.g., a cell producing an antigen-specific antibody 75 that has one or more desired characteristics), extracting mRNA from the lysed cell (e.g., via a bead conjugated with a poly(T) tail); creating cDNA from the mRNA through a reverse transcription polymerase chain reaction using PCR primers specific to amplify the $V_H$ and $V_L$ regions; cloning the $V_H$ and $V_L$ regions into a plasmid containing an immunoglobulin constant region; and transfecting the plasmid into a cell line (e.g., *e. coli*, CHO, HEK, NSO, or other suitable eukaryotic or mammalian cell line) to make a stable antibody-secreting line (or other protein-producing cell line).

Additionally, in some alternative embodiments, the primary sequence of the antibody (or other protein) produced by the selected cells is sequenced. More specifically, in some embodiments, the V-region DNA sequence from selected cells is sequenced, synthesized, and cloned into a plasmid. In this regard, the sequencing, synthesis, and cloning processes can be accomplished in any suitable manner, including, without limitation, through techniques that are commonly known in the art.

In still other embodiments, cells that have been identified as producing a protein of interest (e.g., an antigen-specific antibody) can be grown (e.g., in cell culture media) and then be fused with any other suitable type of cell (e.g., myeloma cells) to form one or more hybridomas. In some such embodiments, the fusion of the cell that is identified as producing a protein of interest with another cell is a deterministic fusion that allows for the creation of a cell line that produces the protein (e.g., antibody) of interest.

U.S. Provisional Patent Application 61/671,499 file Jul. 13, 2012 (hereinafter the "'499 Application"), which is incorporated herein by reference in its entirety, illustrates examples of techniques and devices that can be used to combine the plasmid into which the portion of the DNA sequence (e.g., the V-region DNA sequence) of the antibody-producing cell 210 was placed with a cell of the cell line to be generated. That is, the plasmid into which the DNA sequence of the cell 210 was placed can be the micro-object 1 120 and the cell of a cell line to be generated can be the micro-object 2 122 in the Figures of the '499 Application. In some embodiments, the plasmid into which the DNA sequence of the cell 210 was placed can thus be combined with the cell of a cell line to be generated using any process and/or device illustrated in the Figures of and discussed in the '499 Application for combining the micro-object 1 120 with the micro-object 2 122 to produce the combined micro-object 124. Moreover, in some embodiments, the cell line referenced at step 135 of FIG. 1 of the instant application can be generated generally in accordance with the process 600 or the process 1100 of FIG. 6 or 11 of the '956 Application.

Figure 3A:
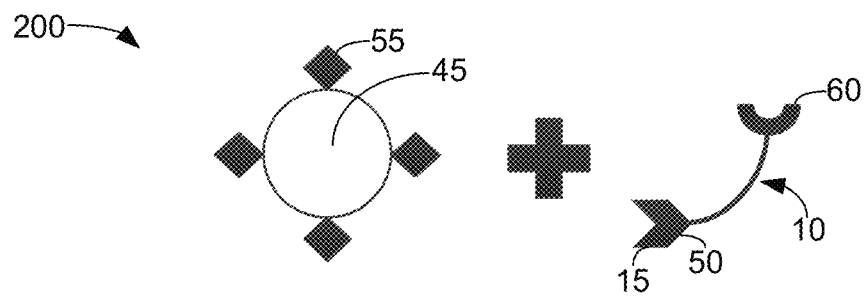
FIGS. 3A-3G depict some embodiments of the method for detecting cells that produce the protein of interest.

With reference now to FIGS. 3A through 3G, those Figures show some embodiments of the described methods in which beads or cells 35 displaying the antigen of interest 40 are used to detect cells that produce an antigen-specific antibody. While the method of FIGS. 3A through 3G can be modified in any suitable manner, FIG. 3A shows that, in some embodiments, the method 200 involves exposing a washed sample of antibody-producing cells 45 to a cross-linking reagent 10 having a first $F_{AB}$ fragment 50 that is specific to a cell surface marker 55 specific to the antibody-producing cells 45 (e.g., CD138 in some embodiments in which the antibody-producing cells comprise plasma cells) and a second $F_{AB}$ fragment 60 that is specific to the antigen of interest 40.

Figure 3B:
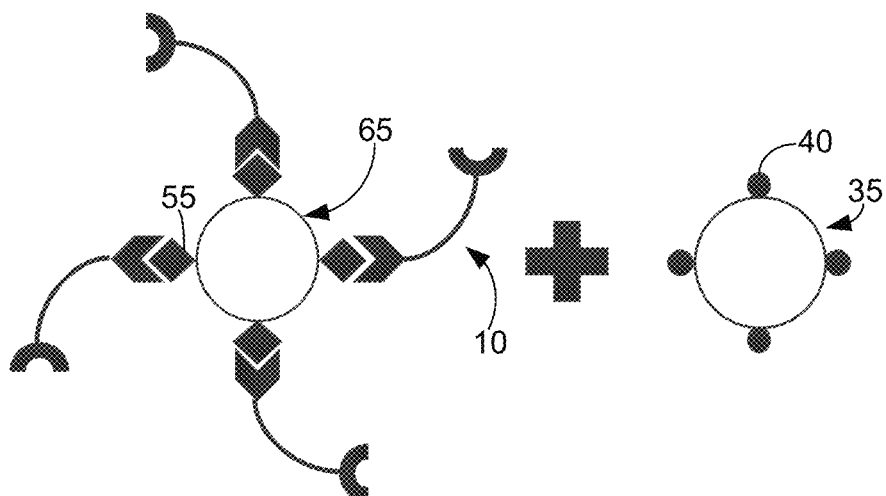
Figure 3C:
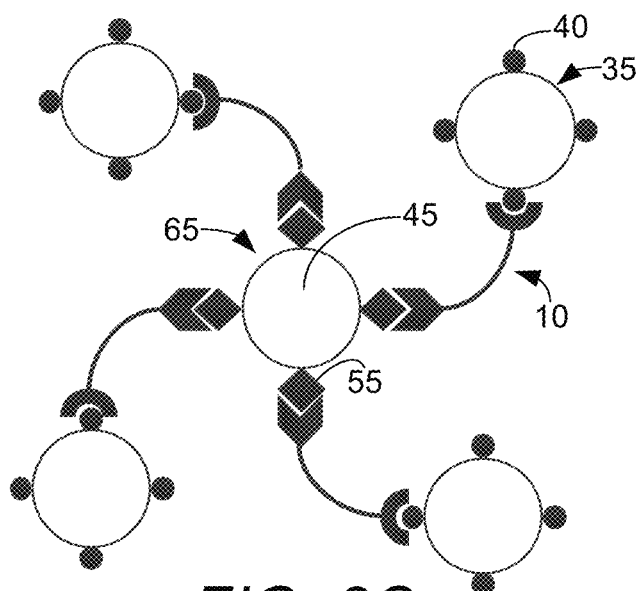

FIG. 3B shows that the tagged cell 65 is then exposed to cells and/or beads 35 that display the antigen of interest 40 on their surface. Accordingly, FIG. 3C shows that the antigen coated cells and/or beads 35 become linked to the antibody-producing cells 45 (e.g., via the cross-linking reagent 10). As discussed above, excess cells/beads 35 are then optionally washed away (e.g., to reduce potential background).

Figure 3D:
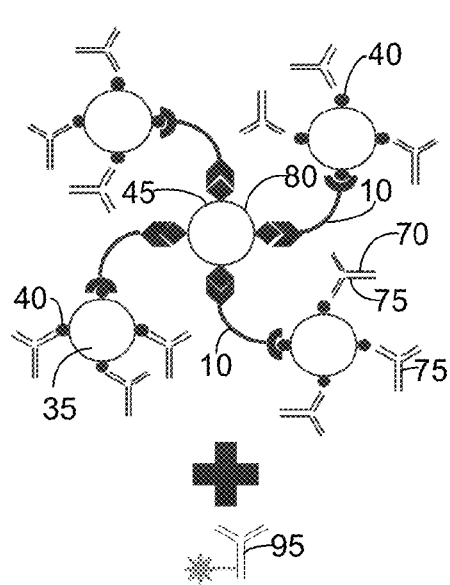

FIG. 3D shows that as the antibody-producing cells 45 are incubated and allowed to produce antibodies 70, the antigen-specific antibody 75 will bind to the antigen of interest 40 that is linked (e.g., via beads/cells 35 and cross-linking reagents 10) to the antibody-producing cells 80 that produce the antigen-specific antibody 75. In contrast, FIG. 3E shows that as cells 85 that produce non-antigen-specific antibodies 90 are incubated and allowed to produce the non-antigen-specific antibody 90, such antibodies do not bind significantly to the antigen of interest 40.

Figure 3E:
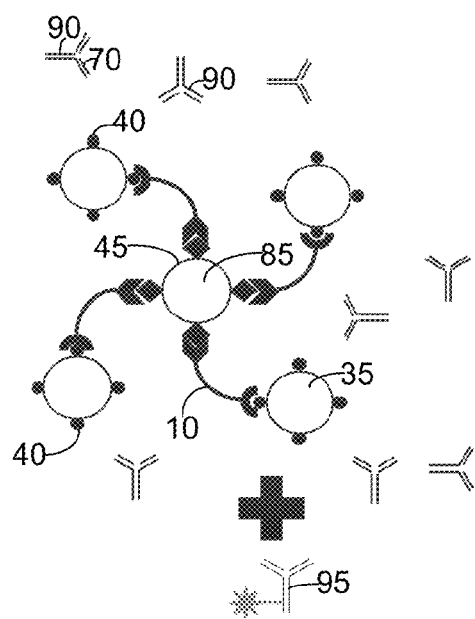
Figure 3F:
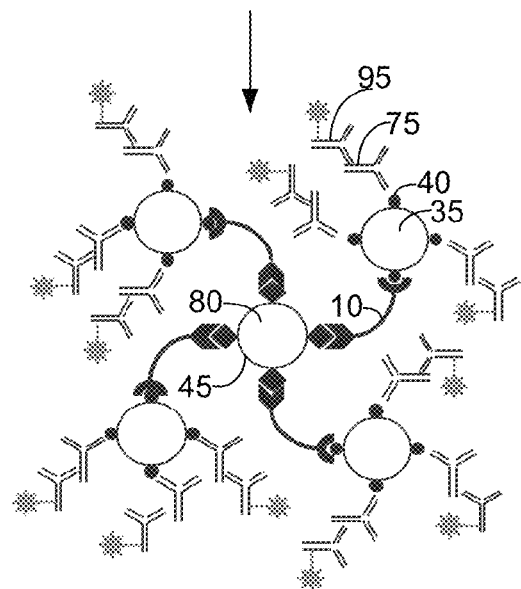
Figure 3G:
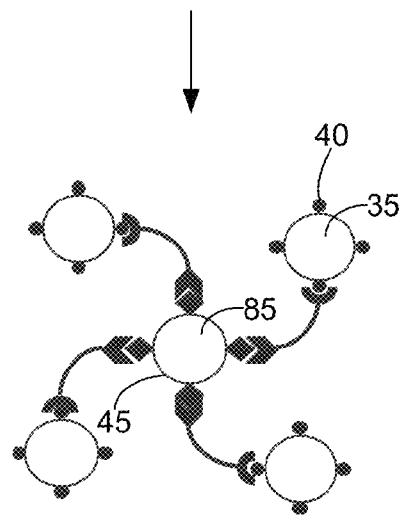

Thus, in some embodiments, when a labeled secondary antibody 95 is added (e.g., a fluorescent labeled anti $F_C$ antibody, as shown in FIGS. 3D and 3E), the secondary antibody is allowed to bind with the antibodies 70 produced by the antibody-producing cells, and antibodies that are not bound to the antigen of interest are optionally washed away. As a result, FIGS. 3F and 3G illustrate that that the cells 80 that produce the antigen-specific antibody 75 are labeled with the labeled secondary antibody 95, such that the labeled antigen-specific, antibody-producing cells (shown in 3F) are easily distinguishable (e.g., via fluorescent microscopy and/or any other suitable method) from the cells 85 that do not produce the antigen-specific antibody (shown in 3G).

Turning now to FIGS. 4A through 4G, those Figures show some embodiments of the described methods in which free-floating antigens 98 are used to detect cells that produce an antigen-specific antibody 75. While the method of FIGS. 4A through 4G can be modified in any suitable manner, FIG. 4A shows that, in some embodiments, the method 300 involves exposing a washed sample of antibody-producing cells 45 to a cross-linking reagent 10 having a first $F_{AB}$ fragment 50 that is specific to a cell surface marker 55 on the antibody-producing cells 45 and a second $F_{AB}$ fragment 60 that is specific to the antigen of interest 40 (e.g., the free-floating antigen 98).

FIG. 4B shows that the tagged cell 65 is then exposed to the free-floating antigen 98. Accordingly, FIG. 4C shows that the free-floating antigen 98 becomes linked to the antibody-producing cells 45 (e.g., via the cross-linking reagent 10). As discussed above, once the free-floating antigen has been linked to the tagged cell, excess free-floating antigen is optionally washed away.

FIG. 4D shows that as the antibody-producing cells 45 are incubated and allowed to produce antibodies 70, the antigen-specific antibody 75 will bind to the antigen of interest 40 (e.g., the free-floating antigen 98) that is linked (e.g., via the cross-linking reagents 10) to the antibody-producing cells 80 that produce the antigen-specific antibody 75. In contrast, FIG. 4E shows that as cells 85 that produce non-antigen-specific antibodies 90 are incubated and allowed to produce antibody 70, such non-antigen-specific antibodies 90 do not bind significantly to the antigen of interest 40 (e.g., antigen 98).

In some embodiments, when a labeled secondary antibody 95 is added to the antibody-producing cells 45 (e.g., a fluorescent labeled anti $F_C$ antibody, as shown in FIGS. 4D and 4E), the secondary antibody is allowed to bind with the antibodies 70 produced by the antibody-producing cells, and antibodies (e.g., non-antigen-specific antibodies 90 and labeled secondary antibody 95 bound thereto) that are not bound the antigen of interest 40 (e.g., antigen 98) are optionally washed away. As a result, FIGS. 4F and 4G illustrate that that the cells 80 that produce the antigen-specific antibody 75 are labeled with the labeled secondary antibody 95, such that the labeled cells (as shown in FIG. 4F) are easily distinguishable (e.g., via fluorescent microscopy and/or any other suitable detection method) from the cells 85 that produce non-antigen-specific antibodies (as shown in FIG. 4G).

With regards now to FIGS. 5A through 5F, those Figures show some embodiments of the described methods in which a cross-linking reagent 10 comprising the antigen of interest 40 is used to detect cells that produce an antigen-specific antibody 75. Although the method of FIGS. 5A through 5F can be modified in any suitable manner, FIG. 5A show that, in some embodiments, the method 400 involves exposing a washed sample of antibody-producing cells 45 to a cross-linking reagent 10 having a first $F_{AB}$ fragment 50 that is specific to a cell surface marker 55 on the antibody-producing cells 45, with the antigen of interest 40 bound to the first $F_{AB}$ fragment 50 through the cross-linker 20.

FIG. 5B shows that once the antibody-producing cells 45 are tagged with the cross-linking reagent 10, the tagged cells 65 are also linked to the antigen of interest 40. As mentioned earlier (e.g., at 130 in FIG. 1), excess cross-linking reagent 10 is then optionally washed away.

FIG. 5C shows that as the tagged antibody-producing cells 65 are incubated and allowed to produce antibodies 70, the antigen-specific antibody 75 will bind to the antigen of interest 40 that is linked (e.g., via the cross-linking reagents 10) to the antibody-producing cells 80 that produce the antigen-specific antibody 75. In contrast, FIG. 5D shows that as cells 85 that produce non-antigen-specific antibodies 90 are incubated and allowed to produce antibody 70, such non-antigen-specific antibodies 90 do not bind, in significant numbers, to the antigen of interest 40.

As a result of the labeling described above, when a labeled secondary antibody 95 is added to the cells 45 (e.g., a fluorescent labeled anti $F_C$ antibody, as shown in FIGS. 5C and 5D), the secondary antibody is allowed to bind with the antibodies 70 produced by the antibody-producing cells, and excess antibodies (e.g., non-antigen-specific antibodies 90 and secondary antibody 95 bound thereto) are optionally washed away. Accordingly, FIGS. 5E and 5F illustrate that the cells 80 that produce the antigen-specific antibody 75 are labeled with the labeled secondary antibody 95, such that the labeled cells (as shown in FIG. 5E) are distinguishable (e.g., via fluorescent microscopy and/or any other suitable detection method) from the cells 85 that produce the non-antigen-specific antibody (shown in FIG. 5F).

As previously mentioned, the described methods can be modified in any suitable manner. In one example (and as previously mentioned above), instead of just being used to identify cells that produce an antigen-specific antibody 75, the described methods can be modified to identify cells that produce any other suitable protein of interest.

While the described systems and methods can be modified in any suitable manner that allows them to be used to identify any suitable protein of interest, FIG. 6 shows some embodiments of one such method 500. In this regard, FIG. 6 shows that, in at least some implementations, the method 500 begins by obtaining a sample containing protein-producing cells. In this regard, this sample can be obtained in any suitable manner (e.g., surgically or otherwise) and from any suitable location (e.g., from an animal's spleen, lymphatic tissue, bone marrow, blood, and/or any other suitable tissue or fluid that may include cells that produce a protein of interest). Furthermore, the sample can contain any suitable number of cells, and the cells can optionally be washed (e.g., in a manner similar to those discussed above with respect to step 115 of FIG. 1 of the instant application).

At 510, FIG. 6 shows the method 500 further includes producing/obtaining one or more cross-linking reagents 20. In this regard, the cross-linking reagents can have any suitable characteristic that allows them to be used to identify a protein of interest (e.g., including, without limitation, any suitable characteristic discussed above with respect to step 110 in FIG. 1 of the instant application). Indeed, in some embodiments, the cross-linking reagent 10 comprises a first portion 15 (e.g., a $F_{AB}$ fragment) that is configured to bind to a cell surface marker on cells (e.g., a specific type of cell) that produce proteins (e.g., a protein of interest, a specific type of protein, etc.). Additionally, in some embodiments, the cross-linking reagent comprises a second portion 25 (e.g., a cross linker 20, a $F_{AB}$ fragment, etc.) that is configured to bind (e.g., directly or indirectly) to a cell, bead, and/or other substrate bearing an antibody specific to the protein of interest (or a protein-specific antibody). In still other embodiments, the second portion of the cross-linking reagent (e.g., the cross linker) is configured to bind directly to the antibody that is specific to the protein of interest.

Continuing with FIG. 6, at 515 the Figure shows that some embodiments of the method 500 include treating the protein-producing cells with any suitable amount (e.g., an excess) of the cross-linking reagent 10 that allows such cells to be tagged with that reagent. In this manner, the first portion 15 of the cross-linking reagent is able to bind to the cell surface markers 55 of the protein-producing cells (e.g., a certain type of protein-producing cells), while leaving cells that do not include the desired cell surface markers substantially untagged.

At 520, FIG. 6 shows that some embodiments of the method 500 further includes allowing the cross-linking reagent 10 to cross react with one or more cells, beads, and/or other substrates that bear an antibody specific to the protein of interest. While this binding can be accomplished in any suitable manner (e.g., by binding the cross-linking reagent to the cells/beads/substrates via a $F_{AB}$ fragment at the second portion 25 of the cross-linking reagent, via the cross-linker 20 itself, or in any other suitable manner), in some embodiments, the cross-linker is bound to the cells/beads/substrates bearing the antibody specific to the protein of interest through the use of a biotin/streptavidin link.

At 525, FIG. 6 shows that, in some embodiments, the tagged protein-producing cells 65 are allowed (e.g., incubated) to produce proteins. As a result, cells that produce the protein of interest will produce proteins that will bind with the antibody on the beads/cells/substrates.

Although the cells that produce the protein of interest can be identified in any suitable manner, FIG. 6 (at 530) shows that, in some embodiments, the method 500 includes treating the tagged cells 65 that are bound to the cells/bead/substrates with a labeled antibody (e.g., an excess amount) that is specific to the protein of interest and that binds to a different epitope than that of the antibody on the cells/bead/substrates. In this regard, the labeled antibody can comprise any suitable label (e.g., one or more luminescent labels, radiolabels, and/or fluorescent labels, such as Aqua, Texas-Red, FITC, rhodamine, rhodamine derivative, fluorescein, fluorescein derivatives, cascade blue, Cy5, phycoerythrin, etc.). In some embodiments, however, the labeled antibody is labeled with one or more fluorescent molecules.

At 535, FIG. 6 shows that some embodiments of the method 500 optionally include the removal of excess labeled antibody. While this removal can be accomplished in any suitable manner, in some embodiments, excess labeled antibody is simply washed away (e.g., as discussed above with respect to step 145 of FIG. 1 of the instant application).

Additionally, through techniques similar to those discussed above with respect to FIG. 1's steps 150, 155, 160, and 165, respectively, FIG. 6's steps 240, 545, 550, and 555 show that, in some embodiments, labeled cells are separated from non-labeled cells, the cross-linking reagent 10 is removed from the protein producing cells, the characteristics of the proteins of interest produced by individual cells are optionally tested, and a cell line producing the protein of interest is optionally created.

Figure 7A:
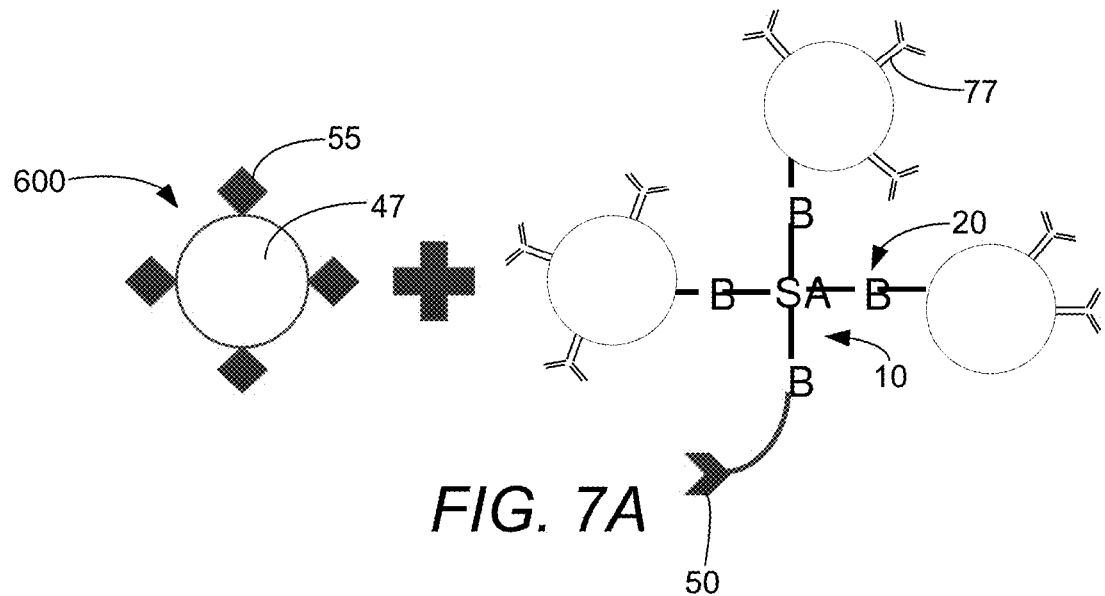
FIGS. 7A-7F depict some additional embodiments of the method for detecting cells that produce the protein of interest.
Figure 7B:
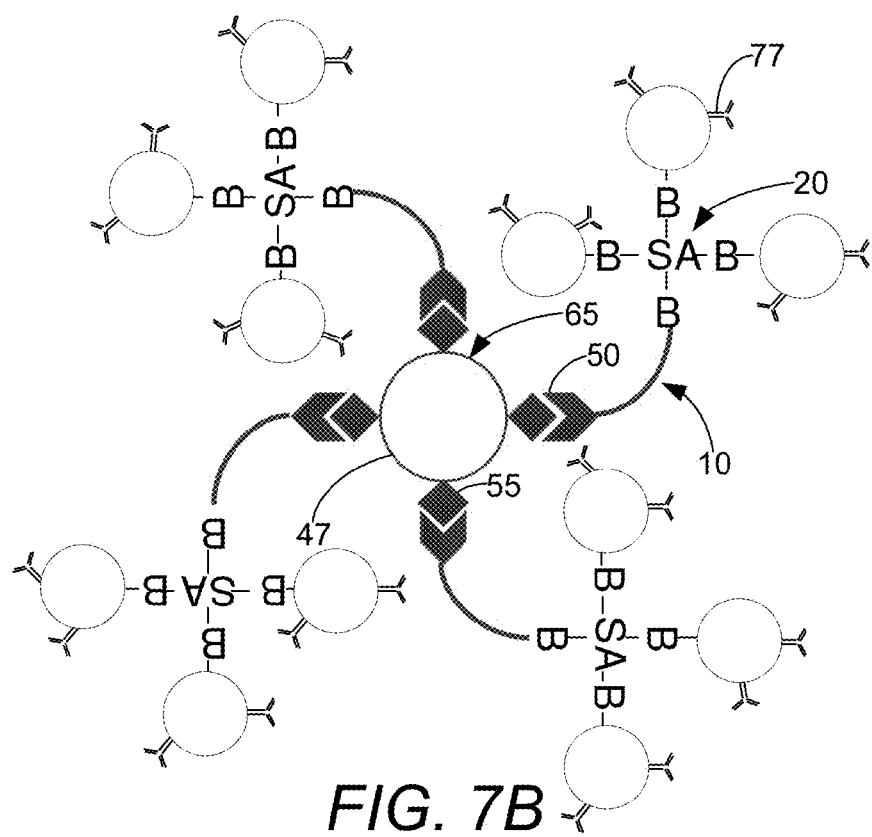

To provide a better understanding of the method 500 described in FIG. 6, FIGS. 7A-7F illustrate some embodiments of a method 600 for identifying cells that produce a protein of interest. In particular, FIG. 7A shows that, in some implementations, the method 600 includes exposing protein-producing cells 47 to a cross-linking reagent 10 having a first portion 15 with specificity for a cell surface marker 55 on cells secreting a protein (e.g., proteins in general, a certain type of protein, the protein of interest, etc.) and a second portion 20 that is configured to react (e.g., via a biotin/streptavidin cross-linker 20) to bead/cells 38 bearing an antibody 77 that is specific to the protein of interest 99. Accordingly, FIG. 7B shows that the protein-producing cells 47 can be tagged (via the cross-linking reagent 10) with cells/beads 38 that bear an antibody 77 specific to the protein of interest 99.

Figure 7C:
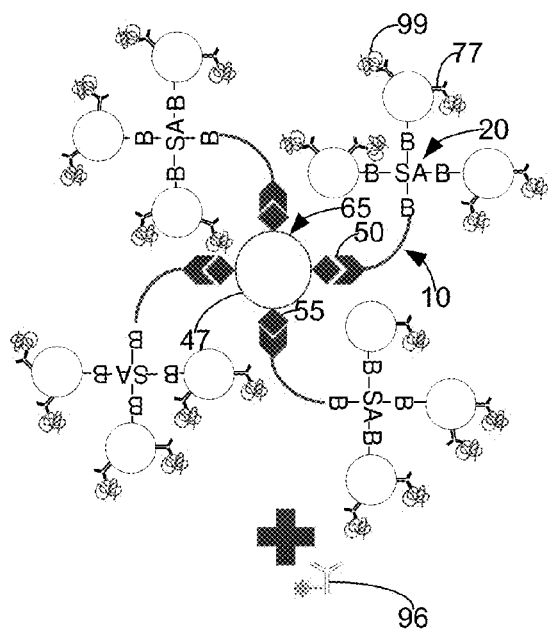
Figure 7D:
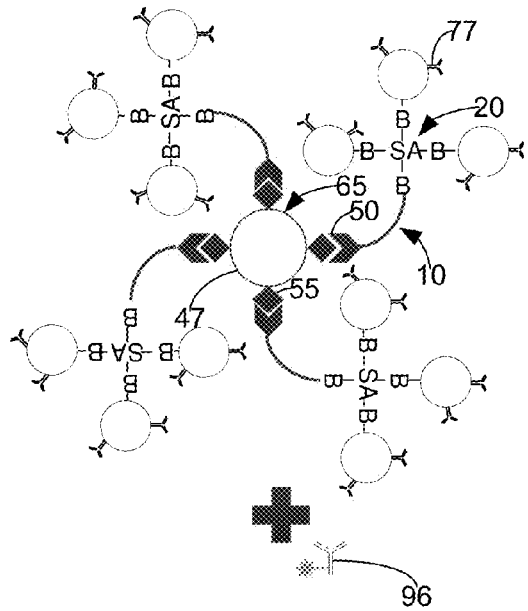

As the protein-producing cells 47 are allowed to secrete proteins, FIG. 7C shows that the cells 48 that produce the protein of interest 99 have a relatively high amount of the protein of interest 99 bind to the antibody 77 bound to the cells/beads 38, at least when compared to cells 49 that do not produce the protein of interest (e.g., as shown in FIG. 7D). In this regard, while the antibody 77 bound to cells 49 that do not produce the protein of interest (e.g., as shown in FIG. 7D) may still bind to the protein of interest 99 released from nearby cells, it is believed that antibodies 77 that are tethered to the cells 48 that produce the protein of interest will bind with a significantly greater amount of the protein of interest than will antibodies that are tethered to cells 49 that do not produce the antigen of interest.

Figure 7E:
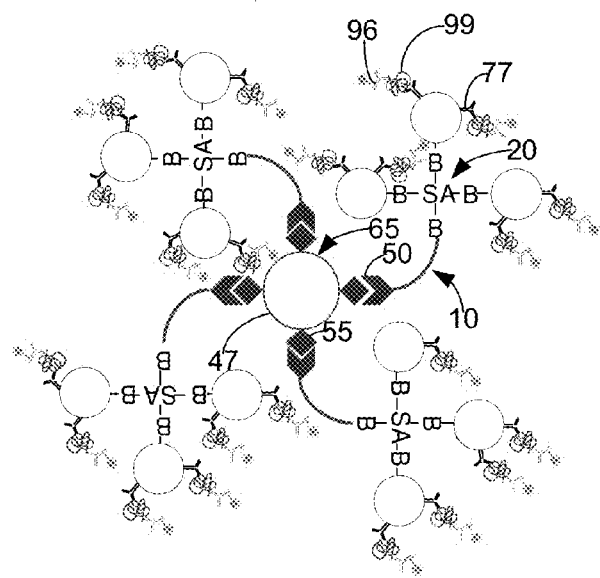
Figure 7F:
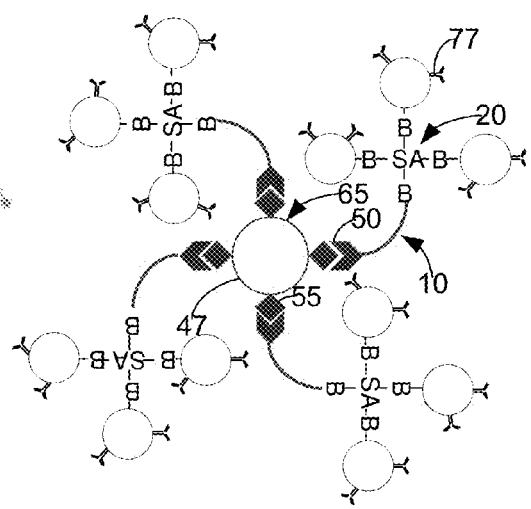

Thus, FIGS. 7E and 7F show that when a labeled antibody 96 that is specific to the protein of interest 99 is added to the tagged cells 65, cells 48 that produce the protein of interest (e.g., as shown in FIG. 7E) are better labeled than cells 49 that do not produce the protein of interest (e.g., as shown in FIG. 7F). As a result of this labeling, the cells that produce the protein of interest will be preferentially labeled and can be separated from other cells with less intense or no labeling. In this regard, the separation can be accomplished in any suitable manner, including, without limitation, through the use of OET, an optoelectronic based method, micromanipulation, microfiltration, etc.

As mentioned previously, the described methods for detecting cells that produce a protein of interest can have several features. By way of example, some embodiments of the described systems and methods allow for individual cells that produce a protein of interest (e.g., an antigen-specific antibody) to be identified and separated from cells that do not produce the protein of interest. In another example, some embodiments of the described methods allow cells that produce a higher amount of a protein of interest to be distinguished (e.g., by the increased intensity of their labeling) from cells that produce a lesser amount or none of the protein of interest.

In still another example, some embodiments of the described methods allow for the identification of cells that secrete a protein of interest, as opposed to cells that express a protein of interest on a membrane surface. In this regard, some conventional methods for identifying cells that express a protein of interest rely on the staining of a cell surface protein of interest. Accordingly, some such conventional methods select for proteins of interest that have been modified post translation in such a way that they are bound to the cellular membrane, rather than identifying proteins of interest that are secreted (as can be accomplished through some embodiments described herein).

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation, and use may be made without departing from the principles and concepts set forth herein. Also, as used herein, the examples and embodiments, in all respects, are meant to be illustrative only and should not be construed as limiting in any manner. Furthermore, where reference is made herein to a list of elements (e.g., elements a, b, c), such reference is intended to include any one of the listed elements by itself, any combination of less than all of the listed elements, and/or a combination of all of the listed elements. Also, as used herein, the terms a, an, and one may each be interchangeable with the terms at least one and one or more. It should also be noted, that while the term step is used herein, that term may be used to simply draw attention to different portions of the described methods and is not meant to delineate a starting point or a stopping point for any portion of the methods, or to be limiting in any other way.

What is claimed:

1. A method for detecting production of an antigen-specific antibody, the method comprising:
    tagging an antibody-producing cell with a cross-linking reagent, wherein the cross-linking reagent comprises a first portion adapted to bind to a cell surface marker that is specific to the antibody-producing cell and a second portion that comprises a protein of interest, wherein the antigen-specific antibody is specific to the protein of interest;
    allowing the antibody-producing cell to produce antigen-specific antibody, such that the antigen-specific antibody binds to the protein of interest; and
    exposing the antibody-producing cell to a labeled secondary antibody configured to specifically bind to the antigen-specific antibody; and
    detecting whether the antibody-producing cell is bound to the labeled secondary antibody.

2. The method of claim 1, wherein the antibody-producing cell is an isolated antibody-producing cell.

3. The method of claim 1, wherein the antibody-producing cell is one of multiple antibody-producing cells in a sample.

4. The method of claim 1, wherein the first portion of the cross-linking reagent comprises a FAB fragment configured to bind to the cell surface marker.

5. The method of claim 1, wherein the first portion of the cross-linking reagent comprises a ligand configured to bind to the cell surface marker, and wherein the ligand does not comprise a FAB fragment.

6. The method of claim 1, wherein the second portion further comprises a substrate to which the protein of interest is bound.

7. The method of claim 6, wherein the second portion is bound to the substrate via a biotin/streptavidin linkage.

8. The method of claim 6, wherein the substrate is a bead, a cell, or a combination thereof.

9. The method of claim 1, wherein the protein of interest is an antibody.

10. The method of claim 1, wherein the labeled secondary antibody is an anti-IgG antibody.

11. A method for detecting production of a protein of interest, the method comprising:
    tagging a protein-producing cell with a cross-linking reagent, wherein the cross-linking reagent comprises a first portion adapted to bind to a cell surface marker that is specific to the protein-producing cell and a second portion that comprises a first ligand, wherein the first ligand specifically binds to the protein of interest;
    allowing the protein-producing cell to produce the protein of interest, such that the first ligand binds to the protein of interest; and
    exposing the protein-producing cell to a labeled antibody configured to specifically bind to the protein of interest; and
    detecting whether the protein-producing cell is bound to the labeled antibody.

12. The method of claim 11, wherein the protein-producing cell is an isolated protein-producing cell.

13. The method of claim 11, wherein the protein-producing cell is one of multiple protein-producing cells in a sample.

14. The method of claim 11, wherein the first portion of the cross-linking reagent comprises a FAB fragment configured to bind to the cell surface marker.

15. The method of claim 11, wherein the first portion of the cross-linking reagent comprises a second ligand configured to bind to the cell surface marker, and wherein the second ligand does not comprise a FAB fragment.

16. The method of claim 11, wherein the first ligand is a protein-specific antibody that specifically binds to the protein of interest.

17. The method of claim 11, wherein the second portion comprises a substrate to which the first ligand is bound.

18. The method of claim 17, wherein the second portion is bound to the substrate via a biotin/streptavidin linkage.

19. The method of claim 17, wherein the substrate is a bead, a cell, or a combination thereof.

20. The method of claim 11, wherein the protein of interest is a hormone, an enzyme, a functional protein, a structural protein, or an antibody.

21. The method of claim 11, wherein the labeled antibody is an anti-IgG antibody.

* * * * *